(12) United States Patent
Daly

(10) Patent No.: US 10,307,707 B2
(45) Date of Patent: Jun. 4, 2019

(54) 1-AMINO-2-METHYL-2-PROPANOL DERIVATIVES

(71) Applicant: Thomas P. Daly, Arlington Heights, IL (US)

(72) Inventor: Thomas P. Daly, Arlington Heights, IL (US)

(*) Notice: Subject to any disclaimer, the term of this patent is extended or adjusted under 35 U.S.C. 154(b) by 0 days.

(21) Appl. No.: 15/981,994

(22) Filed: May 17, 2018

(65) Prior Publication Data

US 2018/0333673 A1 Nov. 22, 2018

Related U.S. Application Data

(60) Provisional application No. 62/507,497, filed on May 17, 2017.

(51) Int. Cl.
| | | |
|---|---|---|
| *C07C 329/14* | (2006.01) |
| *C07C 333/04* | (2006.01) |
| *B01D 53/14* | (2006.01) |
| *C07C 215/06* | (2006.01) |
| *C07F 9/38* | (2006.01) |
| *C07F 9/48* | (2006.01) |
| *C07C 229/24* | (2006.01) |
| *C07C 309/14* | (2006.01) |

(52) U.S. Cl.
CPC ........ *B01D 53/1493* (2013.01); *C07C 215/06* (2013.01); *C07C 329/14* (2013.01); *C07C 333/04* (2013.01); *B01D 2252/20405* (2013.01); *C07C 229/24* (2013.01); *C07C 309/14* (2013.01); *C07F 9/3817* (2013.01); *C07F 9/48* (2013.01)

(58) Field of Classification Search
None
See application file for complete search history.

(56) References Cited

U.S. PATENT DOCUMENTS

| | | | | |
|---|---|---|---|---|
| 7,851,652 B2* | 12/2010 | Daly | ..................... | C07C 215/14 |
| | | | | 562/567 |
| 8,822,728 B2* | 9/2014 | Daly | ..................... | C07C 217/08 |
| | | | | 564/503 |
| 9,447,310 B2* | 9/2016 | Daly | ..................... | C07C 205/15 |
| 9,580,385 B2* | 2/2017 | Daly | ..................... | C07C 333/04 |
| 9,676,709 B2* | 6/2017 | Daly | ..................... | C07C 333/04 |
| 2014/0378433 A1* | 12/2014 | Braun | ................. | C07D 519/00 |
| | | | | 514/211.05 |
| 2015/0246879 A1* | 9/2015 | Daly | ..................... | A01N 25/30 |
| | | | | 544/315 |

(Continued)

OTHER PUBLICATIONS

STN registry file for CAS RN 1491496-52-6 showing compound was entered into STN on Dec. 10, 2013 (Year: 2013).*

(Continued)

*Primary Examiner* — Amy C Bonaparte
(74) *Attorney, Agent, or Firm* — Clifford H. Kraft

(57) ABSTRACT

Amines and amine derivatives that improve the buffering range, and/or reduce the chelation and other negative interactions of the buffer and the system to be buffered. The reaction of amines or polyamines with various molecules to form polyamines with differing pKa's extend the buffering range resulting in polyamines that have the same pKa yields a greater buffering capacity. Derivatives that result in zwitterionic buffers improve yield by allowing a greater range of stability.

3 Claims, 2 Drawing Sheets

(56) References Cited

U.S. PATENT DOCUMENTS

2016/0369142 A1* 12/2016 Daly .................... C07C 205/15

OTHER PUBLICATIONS

STN registry file for CAS RN 1178855-60-1 showing compound was entered into STN on Sep. 1, 2009 (Year: 2009).*
STN registry file for CAS RN 1495434-49-5 showing compound was entered into STN on Dec. 15, 2013 (Year: 2013).*
Mathur ("99mTcN complexes of tert-butyl dithiocarbamate and methoxyisobutyl dithiocarbamate as myocardial and brain imaging agents" Nuclear Medicine Communications, 2005, p. 1013-1019) (Year: 2005).*
STN registry file for CAS RN 1490863-54-1 showing compound was entered into STN on Dec. 9, 2013 (Year: 2013).*
STN registry file for CAS RN 1851169-20-4 showing compound was entered into STN on Jan. 22, 2016 (Year: 2016).*
STN registry file for CAS RN 859980-84-0 showing compound was entered into STN on Aug. 12, 2005 (Year: 2005).*
STN registry file for CAS RN 1179900-21-0 showing compound was entered into STN on Sep. 3, 2009 (Year: 2009).*
STN registry file for CAS RN 1497385-62-2 showing compound was entered into STN on Dec. 17, 2013 (Year: 2013).*

* cited by examiner

G is chosen from -H, -CH3, -CH2CH3, -OH. J is chosen from alkyl, alkenyl, alkynyl, branched or linear, -H, -(CH2CH2O)nH, -(CH2CH2CH2O)nH, -(CH2CH(CH3)O)nH, -(CH2C(CH3)2O)nH. m is 1 or 2, n is an integer greater than zero.

1-AMINO-2-METHYL-2-PROPANOL DERIVATIVES

This application is related to, and claims priority from U.S. Provisional Patent application No. 62/507,497 filed May 17, 2017. Application 62/507,497 is hereby incorporated by reference in its entirety.

BACKGROUND

Field of the Invention

The present invention relates generally to the field of amines and more particularly to a classes of amino zwitterions.

Description of the Problem Solved by the Invention

Amines are extremely useful compounds in the buffering of biological systems. Each class of amine has various limitations which require choosing an amine based on multiple factors to select the best amine. For example, pH buffering range is typically most important, but issues of chelation, pH range stability, and solubility also come into play. Typically, a sub-optimal buffer will result in yields that are well below the potential yield. The present invention improves the yields in fermentation and purification, and improves shelf stability of proteins and amino acids.

SUMMARY OF THE INVENTION

The present invention relates to amines and amine derivatives that improve the buffering range, and/or reduce the chelation and other negative interactions of the buffer and the system to be buffered. The reaction of amines or polyamines with various molecules to form amine derivatives and polyamines and derivatives with differing pKa's extend the buffering range; derivatives that result in polyamines that have the same pKa yield a greater buffering capacity. Derivatives that result in zwitterionic buffers improve yield by allowing a greater range of stability and reduced conductivity. Products of the present invention find uses as gas scrubbers, mining collectors, pigment dispersants as well as other industrial and commercial uses.

DESCRIPTION OF THE FIGURES

Attention is now directed to the following figures that describe embodiments of the present invention.

Several drawings and illustrations have been presented to aid in understanding the invention. The scope of the present invention is not limited to what is shown in the figures.

DETAILED DESCRIPTION OF THE INVENTION

The formation of zwitterions from amines is a useful transformation by allowing a molecule to function as its own conjugate acid or conjugate base. This allows for the elimination of small molecule or atomic counter ions that can adversely effect the ionic strength of the solution. Several transformations are shown that have a wide range of uses including, but not limited to, biological buffering, dispersing pigments and minerals, collecting minerals, buffering fracking fluids, bridging of disparate polymers, gas scrubbing, preventing biological contamination or destruction, and use as surfactants.

Figure 1:
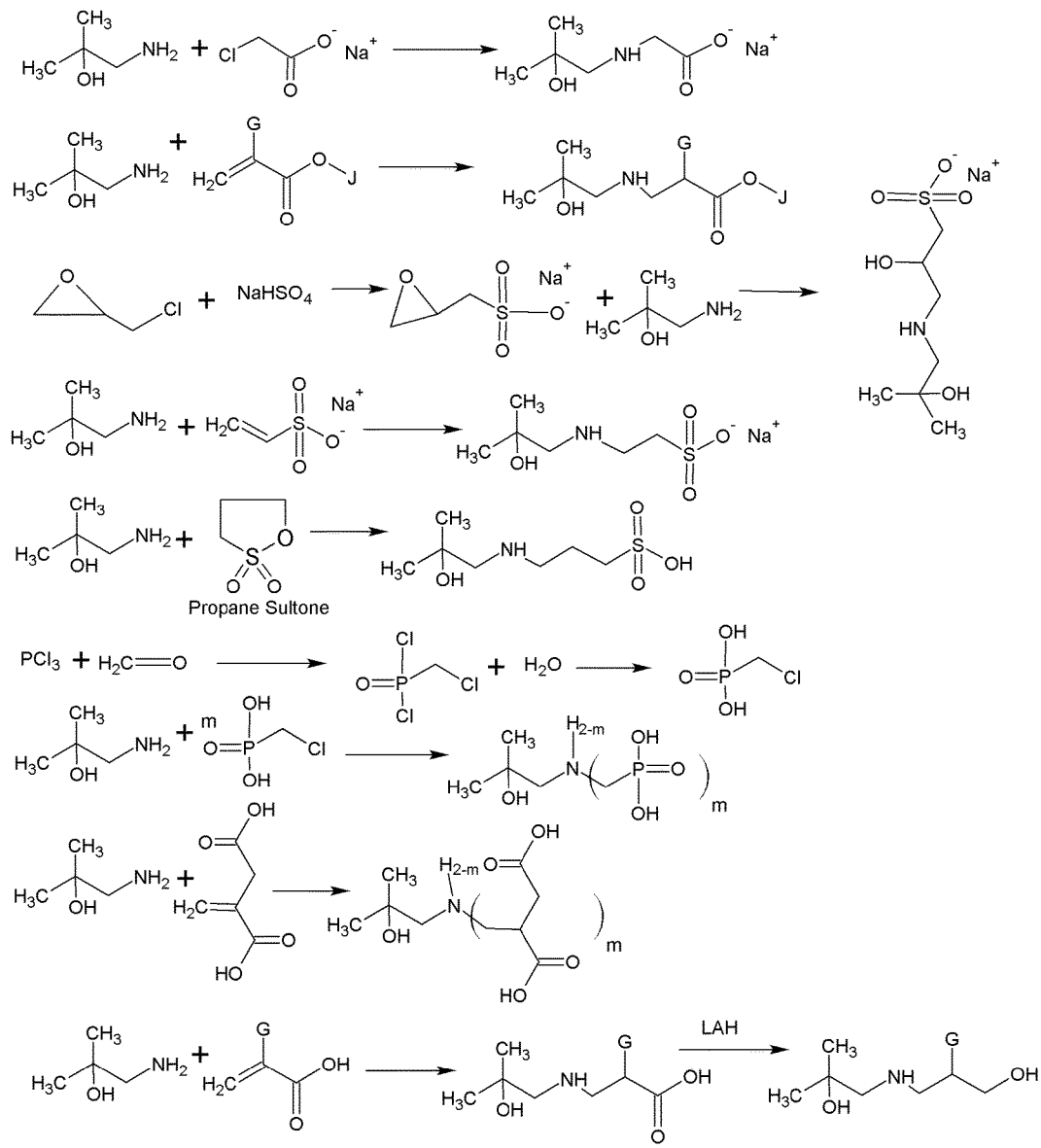
FIG. 1 shows the synthesis of zwitterion type buffers from 1-Amino-2-Methyl-2-propanol.

FIG. 1 shows the synthesis of a range of zwitterions. Each transformation has its own advantages. For example, the carboxcylic acid zwitterions are useful as buffers, but also bridge carboxcylic acid and hydroxyl functional polymers. The sulfonate functional zwitterions are less chelating than the carboxcylic acid functional buffers. The sulfonates derived from sultones form free zwitterions without the need to ion exchange. While only propane sultone is shown, the zwitterions derived from the higher sultones, such as butane sultone, or any other sultone, are within the scope of the present invention. The phosphonates function as scale inhibitors as well as having a buffering capability. The final line of FIG. 1, where $G=\!\!=\!\!-CH_3$ is a particularly good gas scrubbing amine that is selective for $H_2S$.

Figure 2:
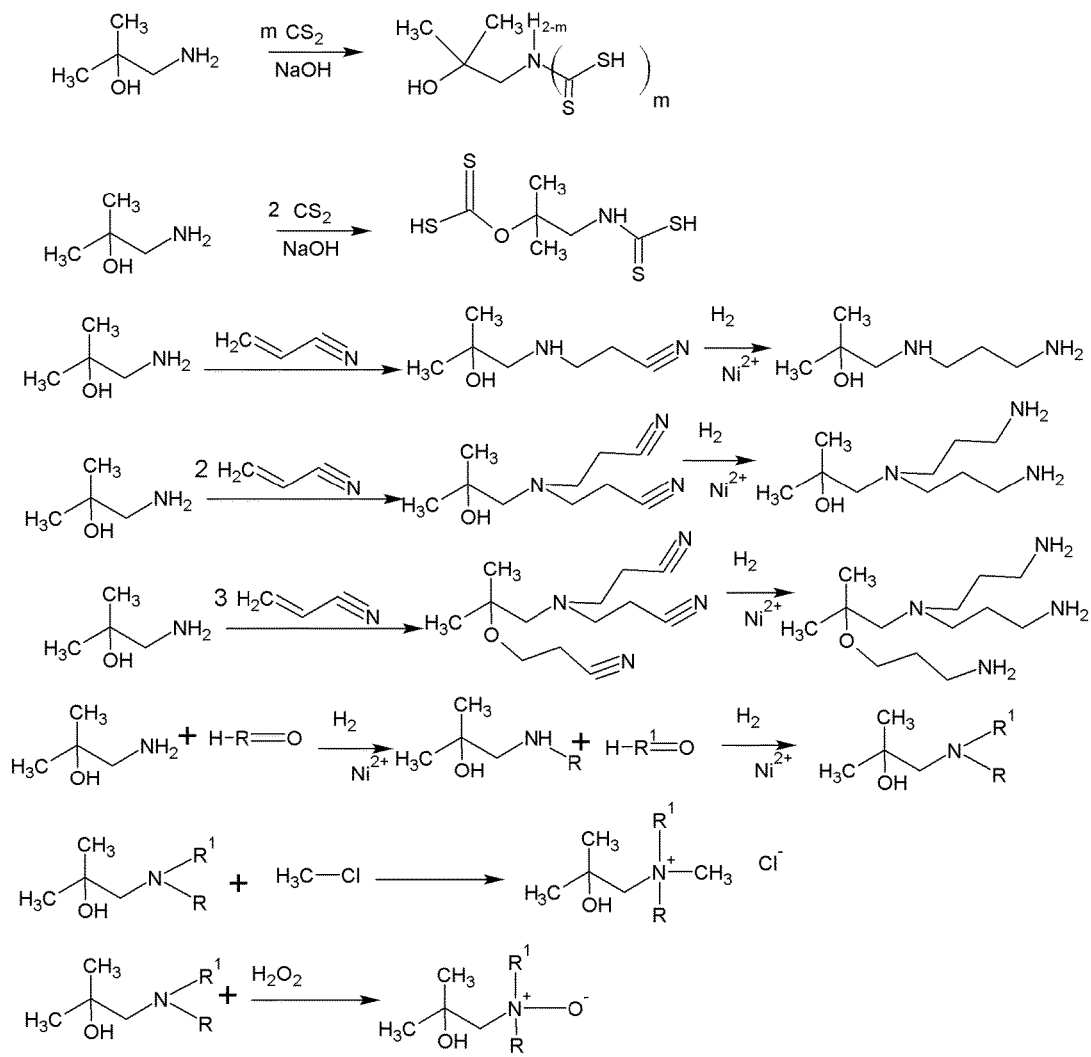
FIG. 2 shows the synthesis of dithicarbamates, dithiocarbamate-xanthates, polyamines, quaternary amines, amine oxides, secondary and tertiary amines.

FIG. 2 shows the synthesis of zwitterions derived from $CS_2$. These zwitterions are excellent mining collectors for sulfide ores and are useful in agriculture as fungicides. The dithiocarbamates and xanthates are not stable in their free form, but are stable as their salts. The scope of the present invention includes all metal and amine salts. The xanthates and dithiocarbamates have additional functionality in agriculture. The traditional uses such as chelants, and dispersants, are complimented by their use as antifungal, antimicrobial as well as growth regulators as promoters and as phytocides and insecticides. Often the effects are more pronounced when the compounds are produced as metal salts, such as zinc, tin, copper or any other transition metal salts. The salts of dicocomethyl amine is particularly useful in agriculture as a fungicide.

The polyamines derived from the reaction with acrylonitrile make excellent bases for polyureas, or polyurea/polyurethane hybrids, where the reactivity difference can be taken advantage of to control pot life, cure rate and open time. The polyamines can either be formed as linear or branched. Linear polyamines are made through the alternating steps of adding one mole of acrylonitrile per primary amino nitrogen followed by reduction with hydrogen in the presence of raney nickel or any other reduction catalyst or reduction method. Branching can be introduced at any point by adding 2 or more moles of acrylonitrile per primary nitrogen and reducing. While the linear diamines are shown, further additions to form linear of branched polyamines are within the scope of the present invention, including the ether amine functionality incorporated through the reaction of the acrylonitrile with the alcohol group. These polyamines can be converted to the polydithiocarbamates through the reaction with $CS_2$. The benefits of doing so include the ability to make powerful polymeric dispersants. The tertiary amines are useful as starting materials for quaternary ammonium compounds and amine oxides which both function as surfactants. The quats can be made from typical quaternizing agents such as methyl chloride, benzyl chloride, dimethylsufate, diethylsulfate, as well as less common quaternizing agents such as ethyl benzyl chloride and chloromethylnaphthalene; all quaternizing agents are within the scope of the present invention.

The tertiary amine where $R=\!\!=\!\!R^1=\!\!=\!\!-CH_3$ is excellent for use in polyurethane dispersions or water reducible alkyds as a buffer or as a vapor phase corrosion inhibitor. The tertiary amines can also be made into amine oxides and betaines. This is typically accomplished by reacting the teriary amines with sodium monochoroacetic acid, acrylic acid or similar acrylic functional molecules such as methacrylic acid. The benefit of the acrylic functional molecules as that a salt free betaine is formed.

The mineral bases such as lime, calcium hydroxide or potassium hydroxide and all others enable the production of the molecules herein disclosed, but without sodium. This is particularly important in agricultural applications. The agricultural applications also benefit from the fatty tertiary amines in that they help the dithiocarbamates or xanthates penetrate the target organism that is to be controlled. The dithiocarbamates can be made with the starting amine as the counter ion. In this case, two molar equivalents of the amine is utilized to one molar equivalent of carbon disulfide during manufacture.

While many of the benefits of these molecules have been recognized in biological systems, the zwitterions and derivatives are also known to be beneficial as dispersants, chelants, cross-linkers, antimicrobials, preservatives of organic systems, as well as pH buffers in oilfield drilling systems and hydraulic fracturing. Additionally, the molecules of the present invention find utility as collectors in mining and as depressants. Further, in ball milling, the dispersant characteristics improve the characteristics of ore pellets. The zwitterionic molecules of the present invention also find utility in high energy storage systems, such as lithium ion and lithium polymer batteries as a means of improving charge transport and as acting as a salt bridge in other battery applications. In addition, these compounds find application as asphat antistrip.

Several descriptions and illustrations have been presented to enhance understanding of the present invention. One skilled in the art will know that numerous changes and variations are possible without departing from the spirit of the invention. Each of these changes and variations are within the scope of the present invention.

I claim:

1. A mining collector of the following structure:

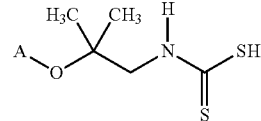

and salts thereof,
wherein A is chosen from —CS$_2$H or —H.

2. The mining collector and its salts of claim 1 wherein A=-H.

3. The mining collector and its salts of claim 1 wherein A=-CS$_2$H.

* * * * *